United States Patent [19]
Laties et al.

[11] Patent Number: 5,122,522
[45] Date of Patent: Jun. 16, 1992

[54] TREATMENT AND CONTROL OF OCULAR DEVELOPMENT

[75] Inventors: Alan M. Laties, Philadelphia; Richard A. Stone, Havertown, both of Pa.

[73] Assignee: The Trustees of the University of Pennsylvania, Philadelphia, Pa.

[21] Appl. No.: 522,241

[22] Filed: May 11, 1990

Related U.S. Application Data

[63] Continuation-in-part of Ser. No. 369,293, Jun. 21, 1989, abandoned.

[51] Int. Cl.$^5$ .............................................. A61K 31/55
[52] U.S. Cl. .................................... 514/220; 514/912
[58] Field of Search ............................... 514/342, 220

[56] References Cited

U.S. PATENT DOCUMENTS 4,616,025 10/1986 Ezer et al. ........................... 514/342

OTHER PUBLICATIONS

Chem Abst. 101:33056e (1984) Daniotti et al.
S. D. Meriney et al., J. Neuro. Sci. Dec. 1987 pp. 3827-3839, "Cholinergic Innervation of the Smooth Muscle Cells in the Ceroid Coat of the Chick Eye and its Development".
R. Hammer et al., TIPS Jan. 1982, "Selective Muscarinic Receptor Antagonists".
H. A. Perr et al., Gastroenterology (1989) 96:1521-8, "Cyclic Nucleotides Regulate Collagen Production by Human Intestinal Smooth Muscle Cells".
Scandinavian Journal of Gastroenterology, Papers published on Jun. 8, 1980 on "Advances in Basic and Clinical Pharmacology of Pirenzepine".
Heathcote et al. (Scand. J. Gastro. 1980) "Pirenzepine Selectively Inhibits Gastric Acid Secretion: a Comparative Pharmacological Study Between Pirenzepine and Seven Antiacetylcholine Drugs."
Birdsall et al. (Scand. J. Gastro 1980) "Pirenzepine—a Ligant with Original Binding Properties to Muscarinic Receptors".
Jaup, Stockbrugger and Dotevall. (Scand. J. Gastro 1980) "Comparison of the Action of Pirenzepine and L-Hyoscyamine on Gastric Acid Secretion and Other Muscarinic Effects".
Jaup and Blomstrand, (Scand. J. Gastro. 1980) "Cerebrospinal Fluid Concentration of Pirenzepine After Therapeutic Dosage".
J. J. Hagan et al. (CNS Pharmacology Labs) "The Relative Potencies of Cholinomimetics and Muscarinic Antagonists on the Rat Iris in Vivo": Effects of pH on Potency of Pirenzepine and Telenzepine (1988).
C. Schudt, Euro. Journal of Pharmacology 165 (1989) pp. 87-96, "The Affinity, Selectivity and Biological activity of Telenzepine Enantiomers".
Noel Buckley et al. Am. Soc. for Pharmacology and Experimental Therapeutics 35:469-476 Antagonist Binding Properties of Five Cloned Muscarinic Receptors Expressed in CHO K1 Cells (1989).
Gunter Lambrecht et al. Euro. Journal of Pharmacology 151 (1988) 155-156, "o-Methyoxy-sila-hexocyclium: a New Quarternary $M_1$-selective Muscarinic Antagonist".
Abstract 71.14 by R. A. Stone et al. "Altered Retinal Amine Neurotransmitters in Form-Deprivation Myopia", Soc. Neurosci, Abstr. vol. 13, part I, p. 240, for meeting Nov. 16-21, 1987.
Abstract 36 by R. A. Stone et al., "Altered Dopamine Metabolism and Form-Deprivation Myopia:", Invest. Ophth. Vis. Sci., 29 33, for meeting May 1-6, 1988.
E. Raviola et al., "An Animal Model of Myopia" N.E. Journ. Med. vol. 132, No. 25 (1985).
D. A. Goss. "Attempts to Reduce the Rate of Increase of Myopia in Young People—A Critical Literature Review", Am. Jour. of Optom. & Physc. Optics, vol. 59, No. 10, pp. 828-841 (1982).
B. J. Curtin, "The Myopias—Basic Science and Chemical Management" Harper & Row (1985) pp. 220-225.
M. L. Rubin et al. "Myopia—A Treatable Disease?" Survey of Opthal. vol. 21, No. 1 (Jul.-Aug. 1976).

*Primary Examiner*—Frederick E. Waddell
*Assistant Examiner*—Zohreh A. Fay
*Attorney, Agent, or Firm*—Woodcock Washburn Kurtz Mackiewicz & Norris

[57] ABSTRACT

A composition for the inhibition of the abnormal postnatal axial growth of the eye of a maturing animal which comprises a pharmaceutically effective amount of a muscarinic pharmacological antagonist relatively selective for blocking the cholinergic receptors in cells of the brain, neural tissue and/or neural ganglia but less selective for blocking the cholinergic receptors of the cells of smooth muscles at the front of the eye, said antagonist present in a carrier or diluent suitable for ocular administration. A suitable antagonist is pirenzepine. Other suitable antagonists are telenzepine and o-methoxy-sila-hexocyclium.

3 Claims, No Drawings

TREATMENT AND CONTROL OF OCULAR DEVELOPMENT

GOVERNMENT SUPPORT

Portions of this invention were supported by National Eye Institute grant R01-EY-05454.

REFERENCE TO PRIOR APPLICATION

This application is a continuation-in-part of our prior application Ser. No. 369,293, filed Jun. 21, 1989, now abandoned.

BACKGROUND OF THE INVENTION

This invention relates to control of ocular development and, more particularly, to the treatment of the eye to control the development of myopia (commonly known as nearsightedness).

It has been estimated that about one of every four persons earth suffers from myopia. About one-half or more of these cases are axial myopia, i.e., an elongation of the eye along the visual axis.

At birth, the human eye is about two-thirds adult size and is even at that size relatively short in the axial direction. As a consequence, young children tend to be farsighted. During childhood, as the eye grows, there is a compensatory fine tuning of the optical properties of the cornea and lens to the increasing ocular length. Often the entire process is virtually perfect and no correction is needed for sharp vision at distance; the eye is emmetropic. When regulatory failure in this finely tuned process occurs, it usually goes toward a lengthened eye. As a result, distant images focus in front of the plane of the retina and axial myopia results. If, on the other hand, the regulatory failure leads to an eye whose ocular length is too short, near images focus behind the plane of the retina and the result is hyperopia (commonly known as farsightedness).

Over the years, many theories have been put forth to explain the development of myopia, e.g., inheritance, excessive near work, and environmental influences such as hours of sunshine, diet, etc. From these theories many preventative measures have been proposed including spectacles, eye exercise, eye rest, cycloplegia, and other drug therapies. The clinical literature on the subject is massive.

Based on a theory that substantial use of the eye by children for reading leads to the development of permanent nearsightedness or myopia, many remedies directed at the focussing mechanism at the front of the eye have been proposed. Largely these have been attempts either to block near focus through topical application of drugs or to remove any need for near focus through use of plus lenses that in effect perform the near focus task. Topical drugs that relax the focussing muscle of the eye, the ciliary muscle, are called cycloplegics and have been available for a century.

Some clinical studies have suggested that atropine, a long-acting cycloplegic, applied topically to the eye may retard development of myopia. Atropine treatment, however, is not practical: it causes dilation of the pupil, which results in light sensitivity, and its action to inhibit ocular focussing impairs near visual work like reading. In addition to the discomfort to the patient, there are indications that excess light can harm the retina and questions have been raised concerning the danger of the long-term use of atropine (or other strong cycloplegics) on the retina when exposed to bright light.

There is now substantial evidence to link the posterior part of the eye, specifically image quality at the retina and hence an extension of the nervous system, to the postnatal regulation of ocular growth. There is significant evidence of myopia resulting in an eye that is subjected to retinal image degradation. It has been shown that axial myopia can be experimentally induced, in either birds or primates, in an eye in which the retina is deprived of formed images, e.g., by suturing the eyelids or wearing an image-diffusing goggle. The experimental myopia induced in primates such as monkeys precisely mimics the common axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina.

In the application of R. A. Stone, A. M. Laties and P. M. Iuvone, U.S. application Ser. No. 342,942, filed Apr. 25, 1989, which is a continuation-in-part of Ser. No. 202,220, filed Jun. 3, 1988, a method of controlling the abnormal postnatal growth of the eye of a maturing animal was found which comprises controlling the presence of a neurochemical, its agonist or antagonist, which neurochemical is found to be changed under conditions during maturation leading to abnormal axial length. Therein it is disclosed that in experimental animals, such as chicks or monkeys, subjected to ocular image deprivation ordinarily leading to the development of myopia, the metabolism of certain retinal neurochemicals is altered leading to changes in retinal concentrations thereof. Specifically, retinal concentrations of dopamine were found to be reduced during such image deprivation and the ocular administration of a dopamine-related agent, e.g., apomorphine, a dopamine agonist, was found to inhibit or actually prevent the axial enlargement of the eye under conditions ordinarily leading to such enlargement.

There have been recent advances made in the understanding of the cholinergic nervous system. Cholinergic receptors are proteins embedded in the wall of a cell that respond to the chemical acetylcholine. They are broadly broken down into nicotinic and muscarinic receptors. In this respect, it is now known that the muscarinic receptors are not all of one type. Recent findings show that there are at least five, if not more, types of cholinergic muscarinic receptors (types $M_1$ through $M_5$). Type $M_1$ receptors are those present in abundance and thought to be enriched in the brain neural tissue and neural ganglia. Other receptors are concentrated in other tissues, such as in heart, smooth muscle tissue, or glands. While many pharmacological agents interacting with muscarinic receptors influence several types, some are known to have a major effect on a single type of receptor with relative selectivity and other agents can have a relatively selective effect on a different single receptor. Still other agents may have a significant effect on more than one or even all types of receptors. A pharmacological antagonist, for the purposes of this discussion, is an agent that effectively blocks the receptor. It is known that pirenzepine, (Gastrozepin, LS 519) 5,11-Dihydro-11-[4-methyl-1-piperazinyl)acetyl]-6H-pyrido[2,3-b][1,4]benzodiazepin-6-one, and its dihydrochloride, are known as anticholinergic, selective $M_1$ antagonists. It is further known that telenzepine, i.e., 4,9-dihydro-3-methyl-4[(4-methyl-(1)piperazine)acetyl]]1OH-thieno-[3,4-b][1,5]-benzodiazepin-10-on, and its dihydrochloride, are also known as anticholinergic selective $M_1$ antagonists reported to be about ten times as potent as pirenzepine. (See Euro. Jour. of Pharmacology, 165 (1989) 87-96.) It is also known that 4-DAMP (4-diphenylacetoxy-N-methylpiperadine methiodide) is a selective antagonist for smooth muscle (ordinarily called $M_3$ type but variously called type $M_2$ or $M_3$, as the current classification of receptors is in flux). It is believed that atropine is an antagonist for all types of cholinergic muscarinic receptors.

SUMMARY OF THE INVENTION

It has been found in accordance with this invention that the growth of an animal's eye can be inhibited or regulated by a muscarinic pharmacological agent of a type particularly effective in brain, neural tissue and/or neural ganglia, which agent is relatively less effective toward most smooth muscles such as occur at the front of the eye and in other locations. This invention is more particularly pointed out in the appended claims and is described in its preferred embodiments in the following description.

DETAILED DESCRIPTION OF THE INVENTION

In the ordinary visual function of the eye of an animal, light forming an image passes through the lens and is received by the retina, a neural tissue embryologically related to the brain. The retina transmits this information to the optic nerve which sends it on to the brain.

Retinal neurochemicals (i.e., neuro-active chemical compounds) are key ingredients in the vision process. Specifically, light forming the image is sensed by the light receptors, the rods and cones, of the retina. These photoreceptors act as transducers changing light energy into electrical and/or chemical signals.

In the regular process of transmitting the image information to the brain, retinal nerve cells, in association with the photoreceptors, release neurochemicals to pass information to adjacent retinal cells as parts of a network in the retina leading to the formulation and qualities of the signals that later go to the brain via optic nerve.

In accordance with this invention, it has been found that the anticholinergic muscarinic antagonist pirenzepine, known to be have a relatively selective affinity to type $M_1$ receptors as in neural structures but relatively low affinity for smooth muscle muscarinic receptors, can be effective in blocking the axial-elongation myopia ordinarily produced by ocular image deprivation in the chick. In separate experiments, it has been noted that topical or systemic administration of pirenzepine has relatively little effect on the iris (i.e., little pupil dilation). Similarly, pirenzepine has relatively little effect on the heart rate or esophageal motility in monkeys or humans.

Telenzepine, an even more potent selective $M_1$ antagonist which shows little affinity for $M_3$ smooth muscle receptors, is another example of an agent which can be used to block axial-elongation myopia in a maturing animal. Because of its greater potency, it may be possible to use smaller amounts of telenzepine to achieve a similar effect to that caused by pirenzepine treatment.

Another muscarinic antagonist that can be used as an agent to block axial-elongation myopia is o-methoxysilahexocyclium, i.e., 4-{([cyclohexylhydroxy(2-methoxyphenyl)silyl]methyl}-1, 1-dimethylpiperazinium methyl sulfate See Euro. Jour. Pharm., 151 (1988) 155-156. This agent often referred to as o-MeSiHC, is known to be an antagonist for $M_1$ muscarinic receptors with substantially less effect on smooth muscle receptors whose selectivity in that respect has been reported to be higher than pirenzepine. Again, this may enable the use of smaller amounts to achieve a similar effect in the inhibition of axial-elongation myopia.

Many other potent antagonists for $M_1$ muscarinic receptors are known. Most, however, like atropine also show substantial effects on $M_3$ smooth muscle receptors. If this effect is significant, the discomfort and disability resulting from their use for ocular treatment render their use impractical, at best, and possibly harmful. Ordinarily, the effect of a muscarinic agent on $M_3$ smooth muscle receptors can be observed by its dilation of the pupil upon ocular administration. If the therapeutically effective amount of the agent applied for treatment results in a dilation of the pupil by 2 mm or more, this side effect is likely to limit its use.

As stated herein, the muscarinic agents for use in this invention are those relatively selective in blocking the type $M_1$ receptors which do not select for the type $M_3$ smooth muscle receptors. In general, a suitable agent will have at least five time greater affinity for $M_1$ receptors than for $M_3$ smooth muscle receptors, preferably more than 10 times greater. Pirenzepine, telenzepine and o-MeSiHC are representative of preferred agents.

The affinity and relative affinity of muscarinic antagonists for $M_1$-$M_5$ receptors can be determined by means known in the art. See Buckley et al., Molecular Pharmacology, 35: 469-476 (1989) for a detailed description of techniques known in the art for determining the antagonist binding properties of five cloned muscarinic receptors. Similarly there are many ways in which to accomplish functional studies to measure $M_1$ sensitivity. For instance, one popular method at present is to use vas deferens of the guinea pig which has an $M_1$ sensitivity. First it is set up so that its tension is measured and a known stimulator such as the $M_1$ agonist McNeil A343 is given to change tension by a predictable amount. Under this condition, the predicted effect of the agonist is first carefully plotted and then the degree to which one or another antagonist blocks this agonist effect is measured. In a specific experiment of this kind, pirenzepine was shown to have a strong blocking effect and thus demonstrable $M_1$ antagonist quality.

For the purposes of comparison in chick myopia, companion experiments were run using the ocular administration of 4-DAMP, a muscarinic antagonist having an affinity profile distinct from pirenzepine; 4-DAMP is recognized for its effect on smooth muscle receptors, e.g., that of the bronchus or ileum. It was found that 4-DAMP does not block the axial-elongation myopia ordinarily produced by image deprivation in the chick. It was found, conversely, in separate experiments in rat and monkey after topical application of effective amounts to the eye that 4-DAMP is a potent dilating agent for the pupil. It is expected that similar muscarinic antagonists effective in blocking the receptors of smooth muscle tissue (e.g., of gut and bronchus) would be similarly effective as pupil dilating agents.

Differences in effect between pirenzepine and 4-DAMP in the chick model of experimental myopia lie at the core of the present invention. Pirenzepine would be expected to be more selective for central nervous system tissues such as brain (and retina) while 4-DAMP would be expected to be more selective for smooth muscle as in ileum or iris. Comparison of the differential ocular effects after local administration versus the profiles of the two drugs are interpreted as independent evidence for the retinal hypothesis for axial myopia in lid-sutured chick. In short, it forms the basis for a claim stating that pirenzepine and like drugs with similar relative selectivity for neural muscarinic receptors can inhibit the development of axial elongation of the eye as witnessed in our chick experimental model, while drugs with selectivity directed strongly at other receptor subtypes, especially in smooth muscle tissue, do not. This invention is now described by the following example thereof:

EXAMPLE

Form-deprivation myopia was induced in day-old White Leghorn chicks under aseptic conditions and other anesthesia by eyelid suture to one eye. The chicks were maintained on a 12 hour light:dark cycle. The sutured eyes were treated with either pirenzepine or 4-DAMP at concentrations listed in Table I or saline solution as a control. Drug was injected daily subconjunctivally during the light cycle. At two weeks of age the animals were sacrificed and axial and equatorial dimensions of unfixed eyes were measured with vernier calipers independently by two observers. Lid-sutured chick eyes treated with 4-DAMP developed axial elongation while those treated with pirenzepine had a virtual blockade of axial elongation. The following table illustrates the effects of drug therapy on the growth of lid-sutured chick eyes. The average increase in axial length is the difference, deprived eye minus contralateral unsutured eye, for the number (n) of animals tested.

TABLE I

| Drug | Dose (µg) | Increased Axial length (mm). | n |
|---|---|---|---|
| pirenzepine | 3.5 | 0.07 | 19 |
| " | 0.35 | 0.18 | 13 |
| " | 0.035 | 0.23 | 10 |
| " | 0.0035 | 0.29 | 10 |
| 4-DAMP | 3.5 | 0.29 | 22 |
| " | 0.35 | 0.36 | 7 |
| Saline solution | — | 0.36 | 30 |

Based on a one-way analysis of variance, there is significant effect on axial length ($p < 0.001$ for pirenzepine at 3.5 µg/day and $p < 0.02$ for pirenzepine at 0.35 µg/day) and no significant difference for the two groups treated with 4-DAMP.

It is expected that the known muscarinic antagonists telenzepine and o-MeSiHC can be used in the above example in place of pirenzepine to obtain similar results in the inhibition of axial growth of the chick during maturation. Because of their reported more potent $M_1$ receptor activity, it is expected that these two agents may be as effective as pirenzepine at lower dosage amounts.

Treatment to inhibit axial-elongation myopia during maturation of an animal can be administered by the use of the agent in eye drops. Indeed, in the vast majority of cases, treatment agents are administered to human eyes by the application of eye drops. Eye drops are typically made up at a concentration of active agent between about 0.5 and 2 percent in the ophthalmic medium. A 1 percent solution of pirenzepine (or other agent) in water would be a likely concentration for clinical use. Some constraints in formulation may exist having to do with pH and preservative. A pH of about 6.5 is expected to be acceptable as an ophthalmic drop and practical in terms of known solubility and stability of pirenzepine. Since pirenzepine and telenzepine are known to form very acidic solutions in physiological saline, treatment with known compatible bases to bring the pH up to about 4.5 to 7.5 (preferably 6 or 6.5) is recommended. Phosphate buffering is also common for eye drops and is compatible with pirenzepine and telenzepine. Other additives and ingredients may be present, e.g., those disclosed in Chiou, U.S. Pat. No. 4,865,599, at column 3, lines 7 to 50, which disclosure is incorporated herein by reference. A common regimen for application of eye drops is two to three times a day spaced evenly throughout waking hours. More effective agents may require fewer applications or enable the use of more dilute solutions. Alternatively, ointments, solid inserts and local depositors of powders are now coming into increased use in clinical practice. They avoid problems of drug decomposition while delivering a defined amount of drug. It is, of course, also possible to administer the above-described active agents in therapeutically effective amounts and dosages in pills, capsules, or other preparations for systemic administration.

It should be noted that pirenzepine shares with other tricyclics a good safety profile. It has been reported to be tolerated well in systemic use by most patients with minimal side effects.

Since pirenzepine is generally recognized as remarkably selective for brain and other neural sites, while 4-DAMP is recognized mainly for its functional effect at smooth muscle, the differing results from the application of the two drugs suggest a neural, probably retinal effect as responsible for the blockage of axial elongation. Moreover, it has been found that 4-DAMP has a stronger physiological effect on the anterior segment of the eye whereas pirenzepine has much weaker effects in this regard. On this basis, emphasis is placed on events at the back of the eye as opposed to the front in the genesis of axial elongation. Our present result could in no way be predicted beforehand. The selective action of pirenzepine (sometimes termed an $M_1$ antagonist) toward the blockage of expected axial elongation constitutes the present invention. It is possible that pirenzepine exerts its observed effect by action at a locus other than the retina. For instance, it could directly affect the synthesis of the constituents of the outer-coat of eye, the sclera.

In addition to the aforementioned, we have also found that under certain circumstances local administration of a drug to one eye of a chick with both eyes open (vision unimpeded) causes a selective axial elongation of the treated eye. Specifically we have administered known cholinergic agonists, carbachol (carbamyl choline chloride, i.e., 2-[(aminocarbonyl)]-N,N,N,-trimethylethanammonium chloride), pilocarpine (3-ethyldihydro-4-[(1-methyl-1H-imidazol-5-yl[methyl]-2(3H)-furanone), and the $M_1$ muscarinic agonist McNeil-A-343(the compound (4-hydroxy-2-butynyl)-1-trimethylammonium m-chlorocarbanilate chloride), on a once a day regimen as indicated in Table II below. Each of the drug-treated eyes was longer than its vehicle-treated fellow.

It is common to administer these agents in the form of their salts, e.g., hydrochlorides or nitrates, or less commonly, their esters. The use of an M muscarinic agonist, e.g., McNeil-A-343 is likely to cause less stimulation of the cholinergically sensitive smooth muscles at the front of the eye.

TABLE II

Muscarinic effects on Growth of Open Eyes.

| Drug | Daily Dose ($\mu$g) | Ocular Dimensions (mean ± S.E.M.) drug-treated minus vehicle-treated eye | | n |
|---|---|---|---|---|
| | | Increased Axial Length (mm) | Equatorial Diameter (mm) | |
| carbachol | 0.15 | 0.20 ± 0.03 | 0.07 ± 0.04 | 9 |
| pilocarpine | 2.0 | 0.09 ± 0.04 | −0.004 ± 0.03 | 7 |
| | 0.2 | 0.11 ± 0.03 | −0.02 ± 0.03 | 10 |
| | 0.02 | 0.18 ± 0.08 | 0.05 ± 0.04 | 9 |
| McN-A-343 | 0.3 | 0.18 ± 0.08 | −0.04 ± 0.02 | 10 |

Treatment with 1.5 $\mu$g carbachol produced about 0.14 mm axial increase in 6 treatments.

In addition to the foregoing, tests were run with a combination of an agonist, 0.15$\mu$g carbachol, and an $M_1$ antagonist, 0.3$\mu$g pirenzepine. The results indicated no significant treatment effects on the axial and equatorial length. This is evidence in favor of the finding that $M_1$ muscarinic receptors are involved in stimulation and inhibition of ocular growth.

The increase in axial length observed in the open-eye experiments could be important in the treatment of children with conditions that lead to abnormally small eyes and for individuals with far-sightedness (hyperopia) based on inadequate axial length of the eye.

A description of cholinergic agonists is contained chapter 5 "Cholinergic Agonists" by Palmer Taylor in *Pharmaceutical Basis of Therapeutics*, 7th Ed. Macmillan Publ. (1985) edited by Goodman and Gilman.

In experiments in animals such as those mentioned hereinabove in which axial myopia has been experimentally induced by depriving the retina of formed images, it has been noted by others in primates that amblyopia was also experimentally and coincidentally induced. Amblyopia is evidenced by poor visual acuity in the eye resulting in poor visual performance. Normally, visual acuity improves during maturation. It is known that amblyopia may occur in humans from unknown causes or as part of strabismus. It is possible that administration of therapeutically effective amounts and dosages of the muscarinic antagonists relatively selective in blocking the $M_1$ cholinergic receptors but less selective in blocking cholinergic receptors in smooth muscle cells, e.g., pirenzepine, telenzepine and o-methoxy-sila-hexocyclium, might prevent or inhibit the development of permanent or persistent amblyopia in maturing humans. It is also possible that humans who have already developed amblyopia from other or even unknown causes might be aided by similar therapeutic treatment with the aforementioned agents.

We claim:

1. A method of controlling the abnormal postnatal growth of the eye of a maturing animal which comprises the ocular administration of therapeutically effective amounts of pirenzepine.

2. The method of claim 1 wherein said pirenzepine is administered in a carrier or diluent buffered to a pH suitable for ocular administration.

3. A method of inhibiting the abnormal postnatal axial growth of the eye of a maturing animal during conditions ordinarily leading to said abnormal growth, which comprises administering to said eye during postnatal maturation a therapeutically effective amount of pirenzepine.

* * * * *